United States Patent [19]

Jahn et al.

[11] Patent Number: 4,545,806
[45] Date of Patent: Oct. 8, 1985

[54] 5-(OXO OR THIO HETEROCYCLE) CYCLOHEXANE-1,3-DIONE DERIVATIVES AND THEIR USE FOR CONTROLLING UNDESIRABLE PLANT GROWTH

[75] Inventors: Dieter Jahn, Edingen-Neckarhausen; Rainer Becker, Bad Durkheim; Michael Keil, Freinsheim; Wolfgang Spiegler, Worms; Bruno Wuerzer, Otterstadt, all of Fed. Rep. of Germany

[73] Assignee: BASF Aktiengesellschaft, Fed. Rep. of Germany

[21] Appl. No.: 589,770

[22] Filed: Mar. 15, 1984

[30] Foreign Application Priority Data

Mar. 23, 1983 [DE] Fed. Rep. of Germany ....... 3310418

[51] Int. Cl.⁴ .................... A01N 43/74; A01N 43/40; C07D 213/63; C07D 215/22
[52] U.S. Cl. ........................................ 71/88; 71/90; 71/94; 71/95; 71/96; 546/296; 546/300; 546/219; 546/216; 546/155; 546/157; 546/158; 548/365; 548/363; 548/221; 548/170; 548/485; 548/486
[58] Field of Search ............... 546/296, 300, 219, 216, 546/155, 157, 158; 548/365, 363, 221, 170, 485, 486; 71/90, 95, 96, 94, 88

[56] References Cited

U.S. PATENT DOCUMENTS 4,422,864 12/1983 Becker et al. .................... 71/88

FOREIGN PATENT DOCUMENTS 66195 12/1982 European Pat. Off. ............ 71/94
104876 4/1984 European Pat. Off. ............ 71/94
1461170 1/1977 United Kingdom .

Primary Examiner—Henry R. Jiles
Assistant Examiner—Dale A. Bjorkman
Attorney, Agent, or Firm—Keil & Weinkauf

[57] ABSTRACT

Cyclohexane-1,3-dione derivatives of the formula

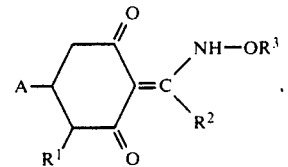

where A is an unsubstituted or substituted, saturated or unsaturated 4-membered to 7-membered heterocyclic structure which contains from 1 to 3 nitrogen atoms and may be fused to an aromatic radical, $R^1$ is hydrogen, methoxycarbonyl, ethoxycarbonyl, methyl or cyano, $R^2$ is alkyl and $R^3$ is alkyl, haloalkenyl or propargyl, and salts of these compounds, are useful for controlling undesirable plant growth.

10 Claims, No Drawings

5-(OXO OR THIO HETEROCYCLE) CYCLOHEXANE-1,3-DIONE DERIVATIVES AND THEIR USE FOR CONTROLLING UNDESIRABLE PLANT GROWTH

The present invention relates to cyclohexane-1,3-dione derivatives and to herbicides which contain these compounds as active ingredients.

It has been disclosed that cyclohexane-1,3-dione derivatives can be used for controlling undesirable grasses in broad-leaved crops (German Laid-Open Application DOS No. 2,439,104).

We have found that cyclohexane-1,3-dione derivatives of the formula

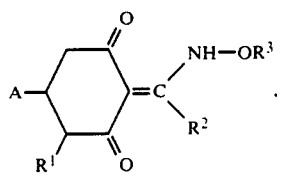

where A is a 4-membered to 7-membered heterocyclic structure which contains from 1 to 3 nitrogen atoms and one or two oxo or thioxo groups, is saturated or unsaturated, may be fused to an aromatic radical and can be substituted by not more than 3 alkyl radicals of not more than 4 carbon atoms, hydroxyl, alkoxy of not more than 4 carbon atoms or unsubstituted or substituted phenyl, $R^1$ is hydrogen, methoxycarbonyl, ethoxycarbonyl, methyl or cyano, $R^2$ is alkyl of 1 to 4 carbon atoms and $R^3$ is alkyl of 1 to 3 carbon atoms, alkenyl of 3 to 4 carbon atoms, haloalkenyl which has from 1 to 3 halogen substituents and where alkenyl is of 3 or 4 carbon atoms, or propargyl, and salts of these compounds have a herbicidal action against grasses and cause little or no damage either to broad-leaved crop plants, monocotyledonous crops which do not belong to the family of the grasses (gramineae) or to wheat.

The compounds of the formula I can occur in a number of tautomeric forms, all of which are embraced by the patent claim:

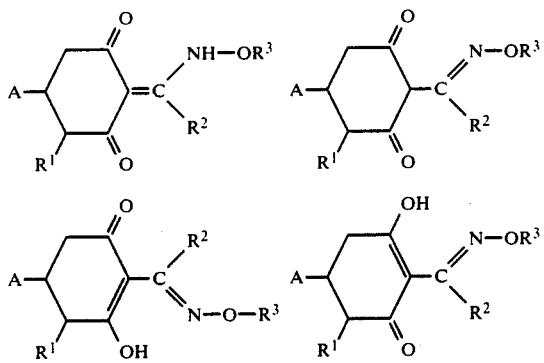

In formula I, A is a 4-membered to 7-membered heterocyclic structure which contains from 1 to 3 nitrogen atoms and one or two oxo or thioxo groups, is saturated or unsaturated, and may be fused to an aromatic radical and can be substituted by not more than 3 alkyl radicals of not more than 4 carbon atoms, hydroxyl, alkoxy of not more than 4 carbon atoms or unsubstituted or substituted phenyl. Examples of A are unsubstituted or substituted 2(1H)-pyridonyl, 2(1H)-pyridinethionyl, piperidonyl, oxoquinolyl, thioxoquinolyl, pyrazolinolyl, oxobenzoxazinyl, oxobenzthiazinyl, oxoindolinyl and pyridyl, in particular 2(1H)-pyridon-2-yl, 1-methyl-2(1H)-pyridon-3-yl, 1-phenyl-2(1H)-pyridon-3-yl, 1-tert.-butyl-2(1H)-pyridon-3-yl, 2-(1H)-pyridinethion-3-yl, 1-methyl-2(1H)-pyridinethion-3-yl, 1-phenyl-2(1H)-pyridinethion-3-yl, 1-tert.-butyl-2(1H)-pyridinethion-3-yl, 6-methyl-2(1H)-pyridon-3-yl, 4,6-dimethyl-2(1H)-pyridon-3-yl, 4-hydroxy-6-methyl-2(1H)-pyridon-3-yl, 1-methyl-4-methoxy-2(1H)-pyridon-3-yl, 1-ethyl-4-ethoxy-2(1H)-pyridon-3-yl, 2-piperidon-3-yl, 2-oxoquinol-3-yl, 2-thioxoquinol-3-yl, 2,3-dimethyl-1-phenyl-3-pyrazolin-5-on-4-yl, 1,2,3-trimethyl-3-pyrazolin-5-on-4-yl, 2,3-dimethyl-3-pyrazolin-5-on-4-yl, 2,3-dihydro-3-oxobenzoxazin-2-yl, 2,3-dihydro-3-oxobenzthiazin-2-yl, 1-methyl-2-oxoindolin-3-yl, 2-oxoindolin-3-yl and 1-methyl-4-methoxy-2(1H)-pyrid-3-yl.

In formula I, $R^2$ is straight-chain or branched alkyl of 1 to 4 carbon atoms, eg. methyl, ethyl, n-propyl, i-propyl, n-butyl, sec.-butyl, i-butyl or tert.-butyl, and $R^3$ is propargyl, alkyl of 1 to 3 carbon atoms, alkenyl of 3 to 4 carbon atoms or haloalkenyl of 3 to 4 carbon atoms which can contain not more than three halogen substituents, eg. methyl, ethyl, n-propyl, i-propyl, n-butyl, sec.-butyl, i-butyl, tert.-butyl, allyl, 1-chloroprop-1-en-3-yl, 2-chloroprop-1-en-3-yl, 1,3-dichloroprop-1-en-3-yl or 1,1,2-trichloroprop-1-en-3-yl.

Examples of suitable salts of the compounds of the formula I are the alkali metal salts, in particular the potassium and sodium salts, the alkaline earth metal salts, in particular calcium, magnesium and barium salts, and manganese, copper, zinc and iron salts, as well as ammonium and phosphonium salts, such as tetraalkylammonium, benzyltrialkylammonium or tetraalkylphosphonium salts, and trialkylsulfonium and trialkylsulfoxonium salts.

Preferred compounds of the formula I are those in which $R^1$ is hydrogen and those in which A is a 2(1H)-pyridinethionyl radical which is substituted by alkyl of not more than 4 carbon atoms, in particular methyl, or by phenyl, as well as salts of these compounds.

The compounds of the formula I can be obtained if a compound of the formula

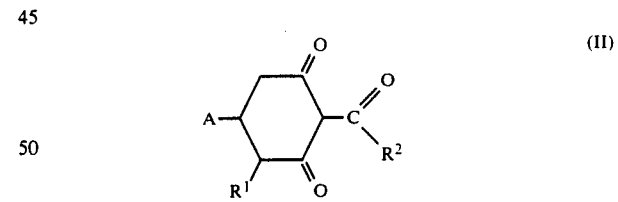

where A, $R^1$ and $R^2$ have the above meanings, is reacted with a hydroxylamine derivative $R^3O-NH_3Y$, where $R^3$ has the above meanings and Y is an anion.

The reaction is advantageously carried out in the heterogeneous phase in an inert diluent at from 0° to 80° C., or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, may also be used.

The reaction proceeds particularly smoothly at a pH of from 2 to 9, in particular from 4.5 to 5.5, the pH advantageously being obtained by the addition of an acetate, for example an alkali metal acetate, in particular sodium acetate or potassium acetate, or a mixture of these. Alkali metal acetates are added in an amount of, for example, from 0.5 to 2 moles per mole of the ammonium compound of the formula $R^3O-NH_3Y$.

Examples of suitable solvents are dimethyl sulfoxide, alcohols, such as methanol, ethanol or isopropanol, benzene, toluene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can be isolated by evaporating down the mixture, adding water, extracting with a non-polar solvent, eg. methylene chloride, and distilling off the solvent under reduced pressure.

The compounds of the formula I can furthermore be obtained by reacting a compound of the formula II with a hydroxylamine of the formula $R^3O-NH_2$, where $R^3$ has the above meanings, in an inert diluent at from 0° C. to the boiling point of the reaction mixture, in particular from 15° to 70° C. If desired, the hydroxylamine can be used in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I can be obtained by treating these compounds with the corresponding alkali metal hydroxides, eg. sodium hydroxide or potassium hydroxide, in aqueous solution or in an organic solvent, such as methanol, ethanol or acetone. The base used may also be a sodium alcoholate or a potassium alcoholate.

The other metal salts, eg. the manganese, copper, zinc, iron, calcium, magnesium and barium salts, can be prepared from the sodium salts by reaction with the corresponding metal chloride in aqueous solution. Ammonium, phosphonium, sulfonium and sulfoxonium salts can be prepared by reacting a compound of the formula I with ammonium, phosphonium, sulfonium or sulfoxonium hydroxide, if necessary in aqueous solution.

The compounds of the formula II can be prepared from cyclohexane-1,3-diones of the formula III, which can also occur in the tautomeric forms IIIa and IIIb

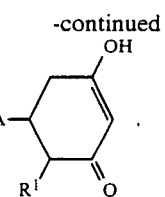
(III)

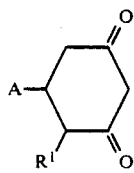
(IIIa)

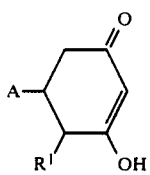
(IIIb)

the preparation being carried out by a conventional method (Tetrahedron Lett. 29 (1975), 2491).

Compounds of the formula II can also be prepared via the enol-ester intermediate, which is obtained, possibly as an isomer mixture, in the reaction of a compound of the formula III, and undergoes rearrangement in the presence of an imidazole or pyridine derivative (Japanese Preliminary Published Application No. 79/063052).

The compounds of the formula III can be obtained by a conventional method, as can be seen from the equations below:

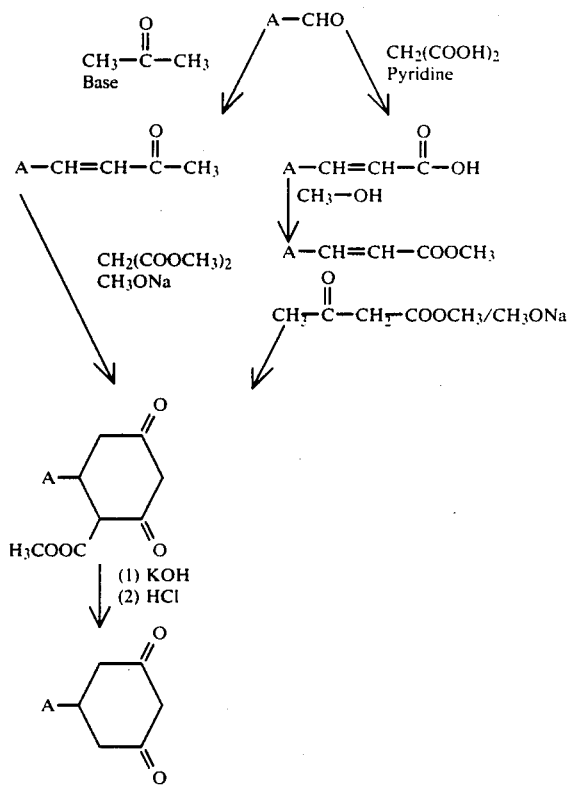

The aldehydes A—CHO, which are used as starting compounds, can be prepared by a conventional method, for example Vilsmeier formylation, oxidation of alcohols, reduction of carboxylic acid derivatives, etc.

The Examples which follow illustrate the preparation of the cyclohexane-1,3-dione derivatives of the formula I. Parts by weight bear the same relation to parts by volume as that of the kilogram to the liter.

EXAMPLE 1

2.1 parts by weight of ethoxyammonium chloride and 1.8 parts by weight of sodium bicarbonate were added to 6.1 parts by weight of 2-butyryl-5-(1-methyl-2(1H)-pyridinethion-3-yl)-cyclohexane-1,3-dione dissolved in 100 parts by volume of methanol. The mixture was stirred for 12 hours at room temperature, after which it was evaporated down under reduced pressure, the residue was stirred with 100 parts of dichloromethane and 100 parts of water, the organic phase was separated off, the aqueous phase was extracted with 50 parts of dichloromethane, and the combined organic phases were washed with water, dried over sodium sulfate and evaporated down under reduced pressure. 2-(1-Ethoxyaminobutylidene)-5-(1-methyl-2(1H)-pyridinethion-3-yl)-cyclohexane-1,3-dione (active ingredient No. 1) of the formula

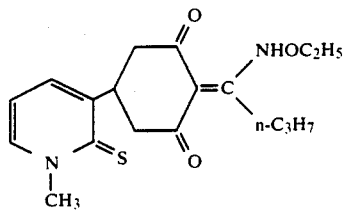

was obtained.

$C_{18}H_{24}N_2O_3S$ (348): Calculated: C 62.04, H 6.94, N 8.04. Found: C 61.9, H 7.0, N 8.3.

$^1$HNMR spectrum in $CDCl_3$, based on tetramethylsilane as an internal standard: 4.05 ppm —O—$CH_2$. 3.90 ppm N—$CH_3$.

EXAMPLE 2

10 parts by weight of 2-butyryl-5-(2-oxoquinol-3-yl)-cyclohexane-1,3-dione, 2.0 parts by weight of ethoxyamine and 100 parts of methanol were stirred for 8 hours at room temperature. The solvent was distilled off under reduced pressure, the residue was taken up in 200 parts of dichloromethane, and the solution was washed with 5% strength hydrochloric acid, dried over sodium sulfate and evaporated down under reduced pressure. 2-(1-Ethoxyaminobutylidene)-5-(2-oxoquinol-3-yl)-cyclohexane-1,3-dione of melting point 155°–157° C. was obtained (active ingredient No. 2).

The following compounds of the formula I are obtained in a similar manner:

| Active ingredient no. | A | $R^1$ | $R^2$ | $R^3$ | $n_D$/m.p. (°C.) |
|---|---|---|---|---|---|
| 3 | 2-oxoquinolin-3-yl | H | n-propyl | allyl | 190–193° C. |
| 4 | 2-oxoquinolin-3-yl | H | n-propyl | propargyl | |
| 5 | 2-oxoquinolin-3-yl | H | n-propyl | —$CH_2$—CH=CHCl | |
| 6 | 1-methyl-2(1H)—pyridinethion-3-yl | H | n-propyl | allyl | |
| 7 | 1-phenyl-2(1H)—pyridinethion-3-yl | H | n-propyl | allyl | 130–133° C. |
| 8 | 1-phenyl-2(1H)—pyridinethion-3-yl | H | n-propyl | ethyl | 147–148° C. |
| 9 | 2-thioxoquinolin-3-yl | H | n-propyl | ethyl | |
| 10 | 2-thioxoquinolin-3-yl | H | n-propyl | allyl | |
| 11 | 2(1H)—pyridon-3-yl | H | n-propyl | allyl | |
| 12 | 2(1H)—pyridon-3-yl | H | n-propyl | ethyl | |
| 13 | 2(1H)—pyridon-3-yl | H | ethyl | ethyl | |
| 14 | 2(1H)—pyridon-3-yl | H | ethyl | allyl | |
| 15 | 1-phenyl-2(1H)—pyridon-3-yl | H | n-propyl | allyl | |
| 16 | 1-phenyl-2(1H)—pyridon-3-yl | H | n-propyl | ethyl | |
| 17 | 1-tert.-butyl-2(1H)—pyridon-3-yl | H | n-propyl | ethyl | |
| 18 | 1-tert.-butyl-2(1H)—pyridon-3-yl | H | n-propyl | allyl | |
| 19 | 2(1H)—pyridinethion-3-yl | H | n-propyl | allyl | |
| 20 | 2(1H)—pyridinethion-3-yl | H | n-propyl | ethyl | |
| 21 | 1-tert.-butyl-2(1H)—pyridinethion-3-yl | H | n-propyl | ethyl | |
| 22 | 1-tert.-butyl-2(1H)—pyridinethion-3-yl | H | n-propyl | allyl | |
| 23 | 6-methyl-2(1H)—pyridon-3-yl | H | n-propyl | allyl | |
| 24 | 6-methyl-2(1H)—pyridon-3-yl | H | n-propyl | ethyl | |
| 25 | 4,6-dimethyl-2(1H)—pyridon-3-yl | H | n-propyl | ethyl | |
| 26 | 4,6-dimethyl-2(1H)—pyridon-3-yl | H | n-propyl | allyl | |
| 27 | 4-hydroxy-6-methyl-2(1H)—pyridon-3-yl | H | n-propyl | allyl | |
| 28 | 4-hydroxy-6-methyl-2(1H)—pyridon-3-yl | H | n-propyl | ethyl | |
| 29 | 4-methoxy-6-methyl-2(1H)—pyridon-3-yl | H | n-propyl | ethyl | |
| 30 | 4-methoxy-6-methyl-2(1H)—pyridon-3-yl | H | n-propyl | allyl | |
| 31 | 1-methyl-4-methoxy-2(1H)—pyridon-3-yl | H | n-propyl | allyl | |
| 32 | 1-methyl-4-methoxy-2(1H)—pyridon-3-yl | H | n-propyl | ethyl | |
| 33 | 1-ethyl-4-ethoxy-2(1H)—pyridon-3-yl | H | n-propyl | ethyl | |
| 34 | 1-ethyl-4-ethoxy-2(1H)—pyridon-3-yl | H | n-propyl | allyl | |
| 35 | piperidon-3-yl | H | n-propyl | allyl | |
| 36 | piperidon-3-yl | H | n-propyl | ethyl | |
| 37 | 2,3-dimethyl-1-phenyl-3-pyrazolin-5-on-4-yl | H | n-propyl | ethyl | |
| 38 | 2,3-dimethyl-1-phenyl-3-pyrazolin-5-on-4-yl | H | n-propyl | allyl | |
| 39 | 2,3-dimethyl-1-phenyl-3-pyrazolin-5-on-4-yl | methoxycarbonyl | n-propyl | ethyl | |
| 40 | 2,3-dimethyl-1-phenyl-3-pyrazolin-5-on-4-yl | methoxycarbonyl | n-propyl | allyl | |
| 41 | 2,3-dimethyl-1-phenyl-3-pyrazolin-5-on-4-yl | H | ethyl | allyl | |
| 42 | 2,3-dimethyl-1-phenyl-3-pyrazolin-5-on-4-yl | H | ethyl | ethyl | |
| 43 | 1,2,3-trimethyl-3-pyrazolin-5-on-4-yl | H | n-propyl | ethyl | 132 |
| 44 | 1,2,3-trimethyl-3-pyrazolin-5-on-4-yl | H | n-propyl | allyl | 98–100 |
| 45 | 2,3-dimethyl-3-pyrazolin-5-on-4-yl | H | n-propyl | allyl | |
| 46 | 2,3-dimethyl-3-pyrazolin-5-on-4-yl | H | n-propyl | ethyl | |

-continued

| Active ingredient no. | A | $R^1$ | $R^2$ | $R^3$ | $n_D$/m.p. (°C.) |
|---|---|---|---|---|---|
| 47 | 2,3-dihydro-3-oxobenzoxazin-2-yl | H | n-propyl | ethyl | |
| 48 | 2,3-dihydro-3-oxobenzoxazin-2-yl | H | n-propyl | allyl | |
| 49 | 1-methyl-2-oxoindolin-3-yl | H | n-propyl | allyl | |
| 50 | 1-methyl-2-oxoindolin-3-yl | H | n-propyl | ethyl | |
| 51 | oxoindolin-3-yl | H | n-propyl | ethyl | |
| 52 | oxoindolin-3-yl | H | n-propyl | allyl | |
| 53 | 1,2,3-trimethyl-3-pyrazolin-5-on-4-yl | H | n-propyl | propargyl | |
| 54 | 2,3-dimethyl-1-phenyl-3-pyrazolin-5-on-4-yl | H | n-propyl | propargyl | |

$^1$H-NMR spectroscopic data, based on tetramethylsilane as internal standard, in CDCl$_3$ as solvent (s=singlet, d=doublet, t=triplet, q=quartet):

| Active ingredient no. | Chemical shift (ppm) |
|---|---|
| 6 | 0.98 (t), 4.02 (s) 4.50 (d), 7.70 (d) |
| 24 | 1.00 (t), 2.38 (s), 6.08 (d) |
| 37 | 1.30 (t), 2.20 (s), 3.05 (s), 7.45 (m) |
| 38 | 2.20 (s), 4.55 (d), 7.45 (m) |
| 39 | 2.20 (s), 3.05 (s), 4.10 (q) |
| 41 | 1.0 (t), 2.20 (s), 3.0 (s), 4.55 (d), 7.45 (m) |
| 42 | 1.33 (t), 2.20 (s), 3.0 (s), 4.10 (q) |
| 43 | 2.10 (s), 3.20 (s), 4.05 (q) |
| 44 | 2.10 (s), 3.20 (s), 3.30 (s), 4.55 (d) |
| 53 | 1.0 (t), 2.12 (s), 3.22 (s), 4.70 (d) |
| 54 | 0.98 (t), 2.55 (d), 4.65 (d), 7.43 (m) |

The cyclohexane-1,3-dione derivatives of the formula I and the salts thereof, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood flour, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 6 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 7 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 2 is intimately mixed with 97 parts by weight of particulate kaolin. A dust is obtained containing 3% by weight of the active ingredient.

VII. 30 parts by weight of compound no. 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.025 to 3 kg/ha, but is preferably from 0.1 to 1.5 kg/ha.

The action of cyclohexane-1,3-dione derivatives of the formula I, and salts thereof, on the growth of plants from the Gramineae family and of broadleaved crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles.

The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. No covers were placed on the pots in this treatment method. The application rates for postemergence treatment varied from 0.25 to 1.0 kg of active ingredient per hectare.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alopecurus myosuroides*, *Avena fatua*, *Avena sativa*, Bromus spp., *Glycine max.*, *Lolium multiflorum*, *Triticum aestivum*, *Hordeum vulgare*, *Setaria italica*, *Beta vulgaris*, *Gossypium hirsutum*, *Sorghum bicolor*, *Sorghum halepense*, and *Zea mays*.

On preemergence application, for example compounds nos. 1, 2, 6 and 7 proved to be herbicidally effective on plants from the Gramineae family.

On postemergence application, for example compound no. 1 selectively combatted unwanted grasses in crop plants such as soybeans and wheat. Compound no. 6 was also selective in cereals. Compound no. 2 was also effective postemergence on grass species, and also on certain crop grasses without damaging the crop grass wheat. Broadleaved crop plants, such as sugar beets, soybeans and cotton, were not damaged either.

In view of the tolerance by crop plants and the numerous application methods possible, the compounds according to the invention may be used in a further large number of crops for removing unwanted wild grasses or grassy crop plants growing where they are not desired. The following crops may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |

-continued

| Botanical name | Common name |
| --- | --- |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Phaseolus lunatus | limabeans |
| Phaseolus mungo | mungbeans |
| Phaseolus vulagaris | green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Sesamum indicum | sesame |
| Solanum tuberosum | Irish potatoes |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |

To increase the spectrum of action and to achieve synergistic effects, the cyclohexane-1,3-dione derivatives of the formula I, and their salts, may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, etc.

It may also be useful to apply the cyclohexane-1,3-dione derivatives of the formula I, or herbicidal agents containing them, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexane-1,3-dione derivative of the formula

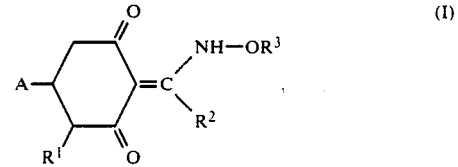

where A is, 2(1-H)-pyridonyl, 2(1H)-pyridinethionyl, piperidonyl, oxoquinolyl, thioxoquinolyl, pyrazolinolyl, oxobenzoxazinyl, oxobenzthiazinyl and oxoindolinyl and said heterocyclic groups substituted by not more than 3 alkyl radicals of not more than 4 carbon atoms, hydroxyl, alkoxy of not more than 4 carbon atoms or unsubstituted phenyl, $R^1$ is hydrogen, methoxycarbonyl, ethoxycarbonyl, methyl or cyano, $R^2$ is alkyl of 1 to 4 carbon atoms and $R^3$ is alkyl of 1 to 3 carbon atoms, alkenyl of 3 or 4 carbon atoms, haloalkenyl which has from 1 to 3 halogen substituents and where alkenyl is of 3 or 4 carbon atoms, or propargyl, and salts thereof.

2. A cyclohexane-1,3-dione derivative of the formula I as defined in claim 1, where $R^1$ is hydrogen, and salts thereof.

3. A cyclohexane-1,3-dione derivatives of the formula I as defined in claim 1, where A is 2(1H)-pyridinethionyl substituted by alkyl of not more than 4 carbon atoms or by phenyl, and salts thereof.

4. A cyclohexane-1,3-dione derivative of the formula I as defined in claim 1, where A is 1-methyl-2(1H)-pyridinethion-3-yl, $R^1$ is hydrogen, $R^2$ is n-propyl and $R^3$ is ethyl, and salts thereof.

5. A herbicidal composition containing inert additives and an effective amount of cyclohexane-1,3-dione derivative of the formula I as defined in claim 1, or a salt thereof.

6. A herbicidal composition as defined in claim 5, containing from 0.1 to 95 wt% of a cyclohexane-1,3-dione derivative of the formula I, or a salt thereof.

7. A herbicidal composition containing inert additives and an effective amount of a cyclohexane-1,3-dione derivative of the formula I as defined in claim 2 or a salt thereof.

8. A herbicidal composition containing inert additives and an effective amount of a cyclohexane-1,3-dione derivative of the formula I as defined in claim 3, or a salt thereof.

9. A process for combatting the growth of unwanted grasses, wherein the unwanted plants or the areas to be kept free from unwanted plant growth are treated with a herbicidally effective amount of a cyclohexane-1,3-dione derivative of the formula I as defined in claim 1.

10. A process for combatting unwanted grasses as set forth in claim 9, wherein the amount of cyclohexane-1,3-dione derivative of the formula I applied is from 0.025 to 3 kg/ha.

* * * * *